United States Patent [19]

Schreiber

[11] 4,187,842
[45] Feb. 12, 1980

[54] PRESSURE MONITOR FOR BREATHING SYSTEM

[75] Inventor: Peter J. Schreiber, Zionsville, Pa.
[73] Assignee: N.A.D., Inc., Telford, Pa.
[21] Appl. No.: 858,041
[22] Filed: Dec. 6, 1977
[51] Int. Cl.$^2$ ............................................. A61M 16/00
[52] U.S. Cl. ............................... 128/202.22; 128/716; 73/756
[58] Field of Search ............... 128/145.5, 145.6, 145.8, 128/188, 204, DIG. 17, DIG. 29, 748, 675, 673, 725, 716; 73/756, 714, 4 R; 200/81.4, 81.5; 137/557; 340/573, 576

[56] References Cited

U.S. PATENT DOCUMENTS

| | | | |
|---|---|---|---|
| 2,893,236 | 7/1959 | Coon et al. | 73/4 R |
| 3,060,744 | 10/1962 | Savage, Jr. | 73/756 |
| 3,333,584 | 8/1967 | Andreasen et al. | 128/145.5 |
| 3,375,721 | 4/1968 | Joesting | 73/756 |
| 3,905,363 | 9/1975 | Dudley | 128/145.8 |
| 3,996,926 | 12/1976 | Birnbaum | 128/673 |

FOREIGN PATENT DOCUMENTS 1161119 8/1969 United Kingdom ................. 128/145.8

Primary Examiner—Henry J. Recla
Attorney, Agent, or Firm—Caesar, Rivise, Bernstein & Cohen, Ltd.

[57] ABSTRACT

A pressure monitor for a breathing system is disclosed which includes three switches, each of which is connected to the breathing system and each of which is preset to be changed in state when the switch is connected to a pressure which is in excess of a predetermined threshold pressure. Each of the switches has a different predetermined threshold with the monitor further including signal means, timing means and selector means. The selector means is connected to one of the switches at a time. The timing means is responsive to the one switch connected to the selector and the signal means is connected to the timing means. The signal means is activated by the timing means whenever the system pressure does not exceed the threshold of the switch connected to the selector means within a predetermined time interval. The selector means includes display means for displaying the threshold pressure of the switch connected to the selector means so that the pressure monitored is readily apparent.

5 Claims, 3 Drawing Figures

PRESSURE MONITOR FOR BREATHING SYSTEM

This invention relates generally to alarms for automatic breathing systems and more particularly to a pressure monitor for a breathing system.

The use of an automatic breathing machine for artificial ventilation of a patient normally bears the hazard of an inadvertant and unnoticed disconnect of the patient. Ventilators are therefore commonly equipped with a device which actuates a visual, audio or visual and audio signal in the event of a disconnect of the patient. The devices are normally comprised of pressure monitors which monitor the ventilation pressure in the breathing circuit delivering the breathing gas to the patient.

The prior art pressure monitors are designed and adjusted to actuate visual or audio or combined alarms in the event that the ventilation pressure within the breathing circuit does not exceed the preset alarm pressure within the preset monitoring time.

Due to the fact that the required maximum ventilation pressure within the breathing circuit varies with lung compliance and air resistance of the patient, the preset alarm pressure of the prior pressure monitors has been adjustable.

That is, in conventional systems the pressure monitor has included a bellows switch which includes a bellows which is connected to the pressure in the breathing system and which expands as the pressure increases. The prior switches include an adjustment means which varies the amount of pressure required in the bellows which will change the state of the switch.

These prior known switches have the disadvantage that the control element for the monitor pressure is not calibrated and marked in values of the monitored pressure. Therefore, there is a considerable time required to adjust the preset pressure of the switch since it takes several breathing intervals to determine whether the preset pressure is high enough to determine that the patient is connected to the breathing machine and low enough so that the alarm does not continually get activated.

However, such time is often not available to the operator of a breathing machine, especially if the unit is used for artificial ventilation during anesthesia.

It is therefore an object of the invention to overcome the aforementioned disadvantages of prior pressure monitors.

Another object of the invention is to provide a new and improved pressure monitor for a breathing system which is quickly adjustable to a known pressure value so that time need not be wasted before the system is in operation.

Another object of the invention is to provide a new and improved pressure monitor for a breathing system which includes a plurality of pressure sensitive switches with known contact pressure which can be alternatively connected to the electronic timing circuit by means of a selector switch.

These and other objects of the invention are achieved by providing a pressure monitor for a breathing system where the monitor includes a plurality of pressure responsive switches, each of which is connected to the breathing system. Each of the switches is preset to be changed in state when the switch is connected to a pressure which is in excess of a predetermined threshold pressure. Each of the switches have a different predetermined threshold and the monitor further includes signal means, timing means and selector means. The selector means includes display means for displaying the threshold pressure of the switch connected to the selector means so that the pressure monitored is readily apparent. The selector means is connectable to one of the switches at a time with the timing means being responsive to the one switch connected to the selector means and the signal means is connected to the timing means. The signal means is activated by the timing means whenever the system pressure does not exceed the threshold of the switch connected to the selector means within a predetermined time interval.

Other objects and many of the attendant advantages of this invention will be readily appreciated as the same becomes better understood by reference to the following detailed description when considered in connection with the accompanying drawing wherein.

Referring now in greater detail to the various figures of the drawing wherein like reference numerals refer to like parts, a pressure monitor is shown generally at 20 in FIG. 1.

Figure 1:
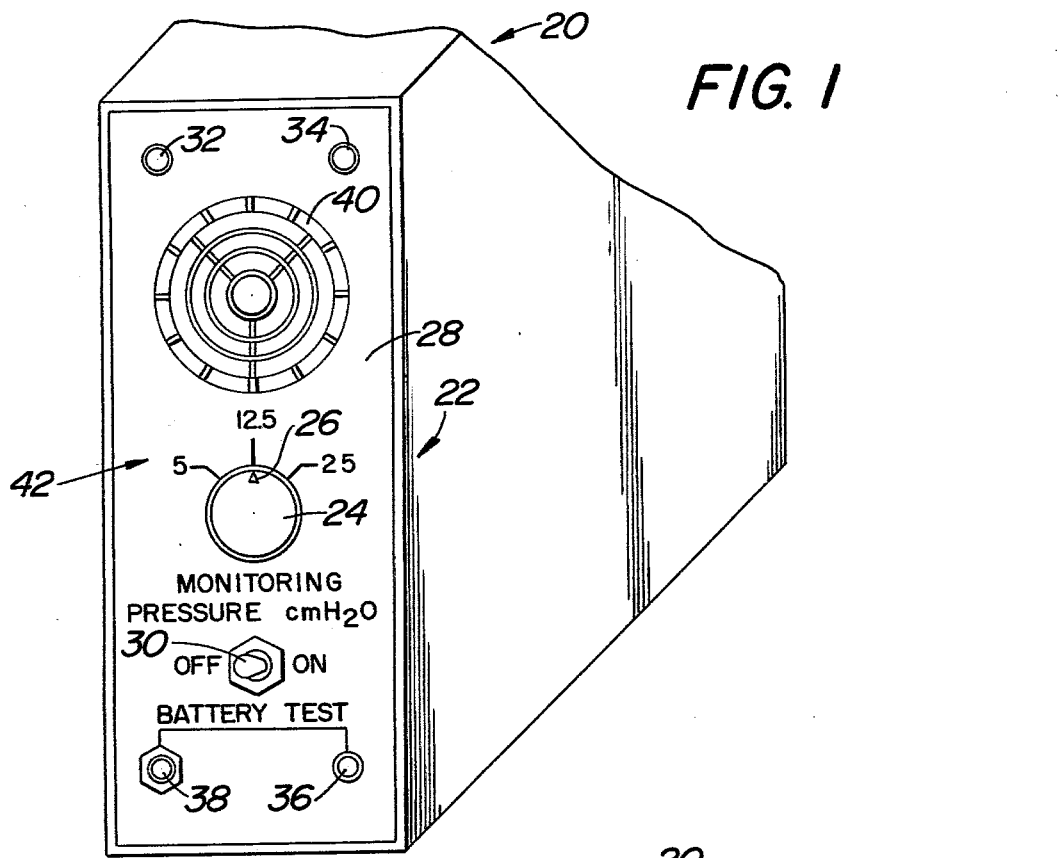
FIG. 1 is a perspective view of a pressure monitor embodying the invention.

The pressure monitor includes selector means 22 having a selector knob 24 which has on the face thereof an arrow 26.

The selector knob 24 is provided in the front wall 28 of the pressure monitor with a power switch 30, a pair of lamps 32 and 34 which are preferably comprised of light emitting diodes, a lamp 36 which also is preferably comprised of a light emitting diode and a push button switch 38. Finally, provided in the front wall 28 above knob 24 is a speaker 40.

The front wall of the pressure monitor 20 also includes indicia 42 which is provided adjacent the knob 24 and is representative of the pressure in centimeters of water (cm $H_2O$). The pressure monitor 20 preferably includes the numerals 5, 12.5 and 25 which represents three settings of pressure of 5 centimeters, 12.5 centimeters and 25 centimeters of water. The knob 24 is rotatable so that the arrow 26 is pointable to one of the three indicia of pressure provided on front wall 28. The indicia act as a display to facilitate operation of the pressure monitor by allowing the visual inspection of the knob 24 to determine the threshold pressure required to activiate the pressure switches inside the monitor which prevents the alarm provided in the unit from being energized.

Figure 2:
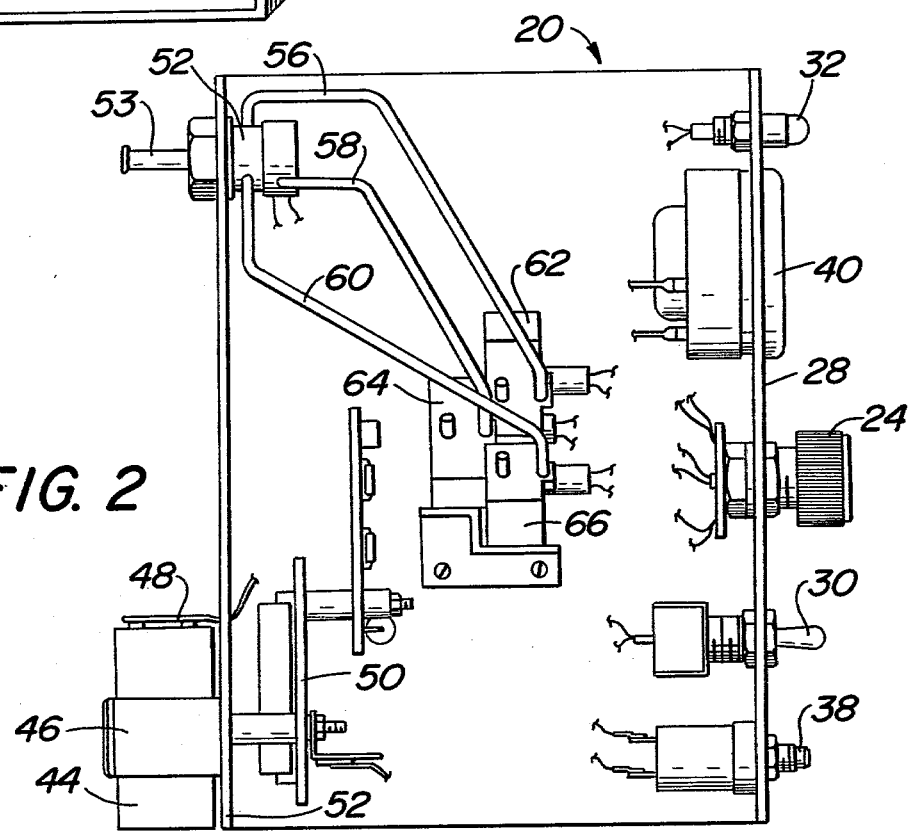
FIG. 2 is a side elevational view of the pressure monitor with the case removed for purposes of clarity.

As best seen in FIG. 2, there is mounted to the back wall of the case of the pressure monitor a power supply 44 in the form of a dry cell battery which is mounted to the rear wall by a suitable bracket 46. A battery connector 48 is connected to the dry cell battery 44 to connect the power of the battery to the circuitry provided within the monitor 20. The circuitry is suitably provided on a printed circuit 50 which is also mounted to the rear wall 52 of the monitor 20.

Mounted above the power source is a manifold 53 which includes a pilot 54 which extends to the breathing system and is connected to the pressure therein.

The manifold also includes three outlet ports which are connected via three tubes 56, 58 and 60 to pressure responsive switches 62, 64 and 66, respectively.

The pressure responsive switches 62, 64 and 66 are connected via the selector means 22 to the power source as will hereinafter be seen in greater detail.

In operation the pressure monitor is connected to the patient via the pilot line 54. The switch 38 is pressed which causes the lamp 36 to be energized if the battery is sufficiently charged.

The power switch 30 is then switched to the ON position. The monitor pressure selector means 22 is then set by rotating the knob 24 to the desired pressure setting which is the next pressure setting below the maximum pressure which is indicated at the breathing system pressure gauge.

For example, where the system pressure is higher than 30 centimeters $H_2O$ the monitoring pressure selector would be rotated so that the arrow would be pointing at the indication of 25 cm $H_2O$.

For a system pressure between 15 and 30 cm $H_2O$ the monitoring pressure selector means is rotated so that the arrow is aligned with the 12.5 cm $H_2O$ indicia.

Finally, for a system peak pressure between 7 and 15 cm $H_2O$, the monitoring pressure selector knob 24 is rotated so that the arrow is aligned with the indicia 5 provided on the front wall 28 of the monitor 20.

Figure 3:
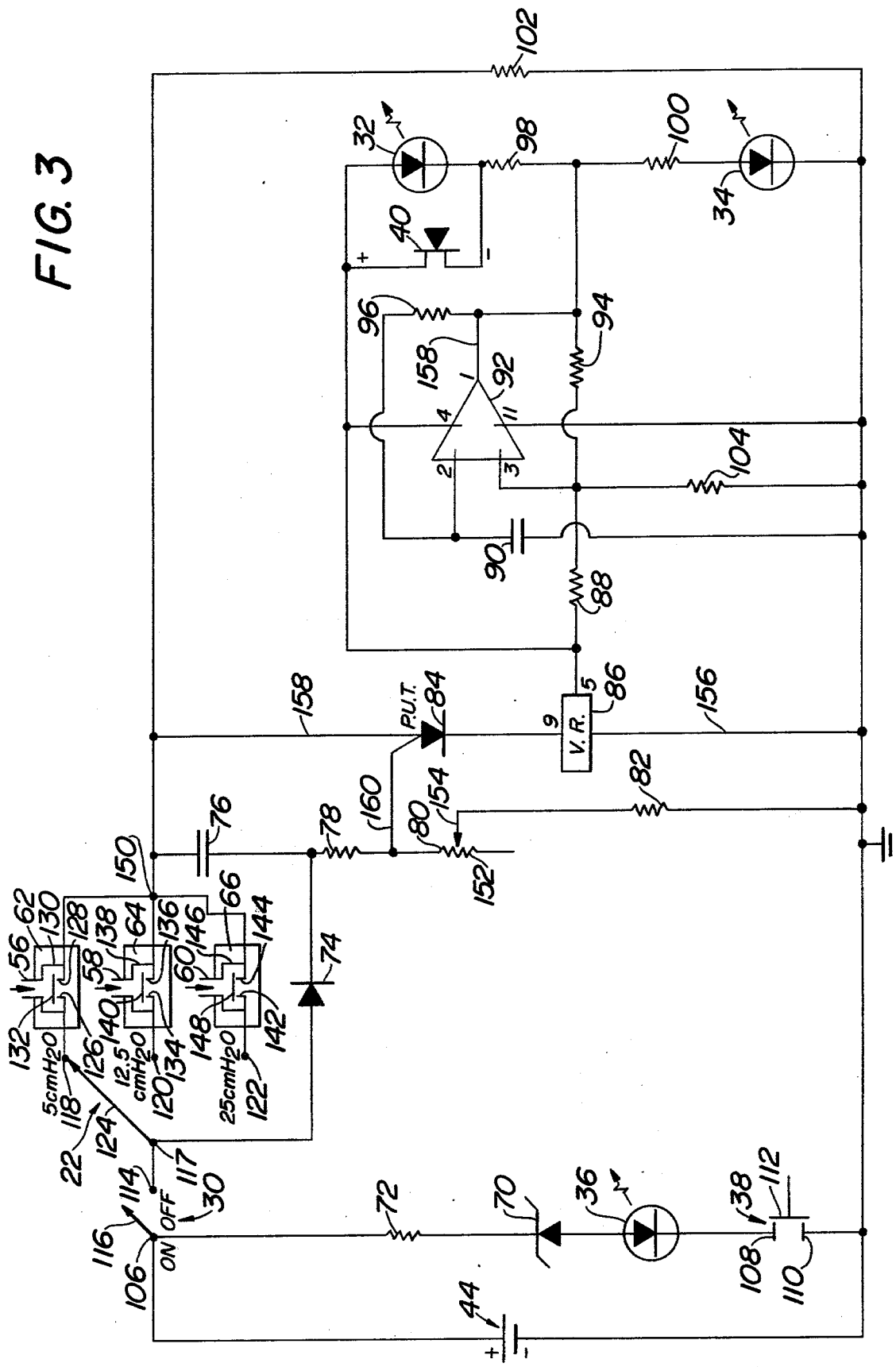
FIG. 3 is a schematic diagram of the circuitry utilized in the pressure monitor.

The circuitry utilized in the pressure monitor is shown schematically in FIG. 3.

The circuitry includes a power switch 30, lamps 32, 34 and 36, push-button switch 38, speaker 40, selector means 22 and battery 44.

In addition, the pressure responsive switches 62, 64 and 66 are also provided. The circuitry includes, in addition to the above, a Zener diode 70, a resistor 72, which are connected serially with the lamp 36 which preferably comprises a light emitting diode (hereinafter referred to as LED).

The circuitry further includes a diode 74, capacitor 76, resistor 78, potentiometer 80, resistor 82, a programmable uni-junction transistor 84 (hereinafter referred to as P.U.T.), voltage regulator 86 (hereinafter referred to as V.R.), resistor 88, capacitor 90, flip flop 92, resistor 94, resistor 96, resistor 98, resistor 100, resistor 102 and resistor 104.

The positive terminal of battery 44 is connected to a first terminal 106 of power switch 30 and to one end of resistor 72. The other end of resistor 72 is connected to the output of Zener diode 70 and the input of Zener diode 70 is connected to the input of LED 36. The output of LED 36 is connected to a first terminal 108 of switch 38.

The second terminal 110 of test switch 38 is connected to the negative terminal of battery 44 and to ground.

The arm 112 of switch 38 closes the circuit between terminals 108 and 110 each time and button of switch 38 is pressed. The closing of the circuit between terminals 108 and 110 thus causes a testing of the battery since the Zener diode 70 has a threshold level of 4.0 volts and thus when battery 44 is at a voltage exceeding 4.0 volts the Zener diode will break down causing conduction therethrough and through the LED 36 causing illumination thereof signifying that the battery is operative whenever the pressing of switch 38 causes the illumination of LED 36.

Switch 30 also includes a terminal 114 and an arm 116. Whenever arm 116 is moved into contact with terminal 114 it causes the conduction between terminals 106 and 114 which acts to provide power to the remaining portion of the circuitry. Terminal 114 of power switch 30 is connected to terminal 117 of selector switch 22.

The switch 22 also includes a plurality of contacts 118, 120 and 122, and a movable arm 124. As the knob 24 of the switch 22 is rotated, the arm 124 is caused to be moved and thereby connect various ones of contacts 118 through 122 to terminal 117.

A first pressure responsive switch 62 includes a pair of terminals 126 and 128, a closed chamber 130 in which a plate 132 is provided which is normally urged away from the contacts 126 and 128 via suitable means such as a spring. The chamber 130 is connected via tube 56 to the breathing system and thereby enables the pressure therein to be transmitted to the pressure responsive switch 62.

The pressure responsive switch 62 is preset so that the plate 132 can be urged against contacts 126 and 128 only when a predetermined pressure or higher pressure has been provided in the closed chamber 130 via tube 56. Similarly, pressure responsive switch 64 includes a pair of terminals 134 and 136 which are provided in a closed chamber 138 having a plate 140. Also, pressure responsive switch 66 includes a pair of terminals 142 and 144 which are provided in closed chamber 146 in which a plate 148 is provided. Each of the pressure responsive switches 62, 64 and 66 are thus closed only when the pressure provided via the tube associated therewith has a pressure which exceeds the threshold pressure of this particular pressure responsive switch.

Thus, for example, pressure responsive switch 62 is preferably calibrated so that the switch is closed when the pressure in chamber 130 exceeds 5 cm $H_2O$. The pressure responsive switch 64 is calibrated to be closed only when the pressure in chamber 138 exceeds 12.5 cm $H_2O$ and pressure responsive switch 66 is calibrated to be closed only when the pressure in chamber 146 exceeds 25 cm $H_2O$.

The contacts 128, 136 and 144 are connected to a common terminal 150. Contact 126 of pressure responsive 62 is connected to contact 118 of switch 22, contact 134 of switch 64 is connected to contact 120 of switch 22 and contact 142 of switch 66 is connected to contact 122.

Terminal 117 is connected to one end of diode 74. The other end of diode 74 is connected to the junction between capacitor 76 and resistor 78. The other end of capacitor 76 is connected to terminal 150, the other end of resistor 78 is connected to one input of P.U.T. 84 and one end of the resistive element 152 of potentiometer 80. The wiper arm 154 of the resistor 80 is connected to resistor 82 which is in turn connected to ground. Terminal 150 is also connected to one base of P.U.T. 84. The output of P.U.T. 84 is connected to the input of the V.R. 86. The output of V.R. 86 is connected to the input of flip flop 92 via resistor 88 and to the input of speaker 40 and LED 32. The flip flop 92 is connected as a multivibrator.

The V.R. 86 is connected via line 156 to ground. The end of resistor 88 connected to flip flop 92 is also connected to one end of resistors 94 and 104. The other end of resistor 94 is connected to LED 32 and speaker 40 via resistor 98 and is connected to the output line 158 of the flip flop 92 and one end of resistor 96. The other end of resistor 96 is connected to one end of capacitor 90 and to an input of flip flop 92. Output line 158 of flip flop 92 is also connected to one end of resistor 100 which is in turn connected to LED 34 which is in turn connected to ground. A load resistor 102 is provided across terminal 150 to ground.

In operation, when the power switch 30 is closed, a positive voltage is provided to one of the contacts 126, 134, or 142 of switches 62, 64 and 66 in accordance with the position of arm 124 of selector switch 22.

The plurality of switches 62, 64 and 66 in combination with selector switch 22 enables one of three discrete predetermined pressures to be used to monitor the pressure in the breathing system to which the monitor is connected. The remaining portion of the circuitry is substantially conventional in that similar circuitry has been used in prior pressure monitors where a single pressure responsive switch has been provided. In the prior switches the pressure responsive switches have not been calibrated for a predetermined pressure, but are rather variable and not calibrated.

In operation, after the switch 30 has been closed, if the pressure responsive switch 62 to which the arm 124 is connected is not closed within fifteen seconds the voltage on line 158 of P.U.T. 84 goes lower than the voltage on line 160 and thereby causes a signal to be provided from P.U.T. 84 to the V.R. 86 which causes energization of flip flop 92. When flip flop 92 is energized it causes an oscillatory signal to be provided to speaker 40 which causes an audio signal and in addition provides a signal through LED 32 and 34 which is visually apparent through illumination of the LEDS.

The 15 second delay in the energization of the flip flop 92 is caused by the RC circuit comprised of resistors 78 and potentiometer 80 and resistor 82 and capacitor 76. The potentiometer 80 enables the adjustment of the circuitry so that a time delay of greater or less than 15 seconds may also be accomplished. The closing of the pressure responsive switch 62 before the 15 second interval has elapsed causes a positive signal to be applied to capacitor 76 which thereby causes the voltage on line 158 to remain higher than the voltage on line 160. After the pressure responsive switch connected to selector means 22 has been opened the voltage on line 158 starts to decay exponentially and if fifteen seconds elapse before the pressure responsive switch is closed again, the flip flop 92 is energized.

It can therefore be seen that the selector means 22 enables the timing circuit and signalling means to be actuable when monitoring any one of a plurality of different pressures.

Moreover, the knob 24 in combination with the indicia 42 provided on the front wall of the pressure monitor enables the user to quickly determine at what pressure the system is being monitored. Therefore adjustment time is eliminated.

Without further elaboration the foregoing will so fully illustrate my invention that others may, by applying current or future knowledge, readily adapt the same for use under various conditions of service.

What is claimed as the invention is:

1. A pressure monitor for a breathing system, said monitor including a plurality of pressure responsive switches each of which is connected to pressure in said breathing system, each of said switches being preset to be changed in state when said switch is connected to a pressure which is in excess of a predetermined threshold pressure, each of said switches having a different predetermined threshold, said monitor further including signal means, timing means and selector means, said selector means connecting one of said switches at a time to said timing means, said timing means being responsive to said one selected switch and said signal means being connected to said timing means, said signal means being activated by said timing means whenever said system pressure does not exceed the threshold of said switch connected to said selector means within a predetermined time interval.

2. The pressure monitor of claim 1 wherein said monitor includes three switches and said selector means includes display means for displaying the threshold pressure of the switch connected to said selector means so that the pressure monitored is readily apparent.

3. The pressure monitor of claim 1 wherein said signal means includes an audible alarm.

4. The pressure monitor of claim 1 wherein said signal means includes a visual alarm.

5. The pressure monitor of claim 1 wherein said signal means includes both an audible alarm and a visual alarm.

* * * * *